United States Patent [19]

Kölbl et al.

[11] Patent Number: 4,647,581

[45] Date of Patent: Mar. 3, 1987

[54] BICYCLIC PESTICIDAL AGENTS

[75] Inventors: Heinz Kölbl, Cologne; Rudolf Gompper, Munich; Wolfgang Behrenz, Overath; Ingeborg Hammann, Cologne; Bernhard Homeyer; Günther Hermann, both of Leverkusen, all of Fed. Rep. of Germany

[73] Assignee: Bayer Aktiengesellschaft, Leverkusen, Fed. Rep. of Germany

[21] Appl. No.: 588,851

[22] Filed: Mar. 12, 1984

Related U.S. Application Data

[62] Division of Ser. No. 427,230, Sep. 29, 1982, abandoned.

[30] Foreign Application Priority Data

Oct. 16, 1981 [DE] Fed. Rep. of Germany ....... 3141119

[51] Int. Cl.$^4$ ...................... A01N 37/34; A01N 43/20
[52] U.S. Cl. ...................... 514/475; 514/519; 514/521; 514/523; 514/525
[58] Field of Search ............... 514/519, 475, 521, 523, 514/525

[56] References Cited

U.S. PATENT DOCUMENTS

| | | | |
|---|---|---|---|
| 2,536,858 | 1/1951 | Swaney et al. | 514/519 |
| 2,546,174 | 3/1951 | Stonecipher | 424/352 |
| 2,635,979 | 4/1953 | Lidov | 514/519 |
| 2,774,783 | 12/1956 | Ardis | 260/465.7 |
| 2,793,975 | 5/1957 | Mark | 514/519 |
| 3,335,166 | 8/1967 | Stansbury, Jr. et al. | 260/464 |

FOREIGN PATENT DOCUMENTS 2077226 10/1971 France .

OTHER PUBLICATIONS

Koremura, C. A., vol. 60 (1964), 5360e.
All references in patent application Ser. No. 427,230, filed 9/29/82.

Primary Examiner—Allen J. Robinson
Attorney, Agent, or Firm—Sprung Horn Kramer & Woods

[57] ABSTRACT

Combating pests with compounds of the formula

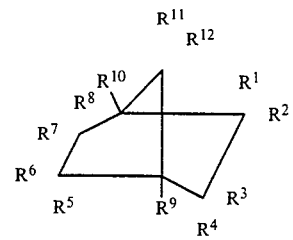

in which the radicals can have many specifically recited definitions. Many of the compounds are novel, particularly those where R' is —CN and R$^2$ is —CN or —CONH$_2$.

7 Claims, No Drawings

BICYCLIC PESTICIDAL AGENTS

This is division of application Ser. No. 427,230, filed Sept. 29, 1982, now abandoned.

The present invention relates to the use as pest-combating agents of certain bicyclic compounds some of which are known and to some of which are new.

It has already been disclosed that highly chlorinated bicyclic compounds possess insecticidal activity (U.S. Pat. No. 2,546,174).

Furthermore, it has been disclosed that 5-nitro-6-trichloromethyl-norbornylene possesses insecticidal activity (Chemical Abstracts vol. 60 reference 5360e).

However, the action of these compounds is not always completely satisfactory, particularly when low concentrations are used.

It has now been discovered that substituted bicyclic compounds of the following general formula (I), some of which are known, can be used as pest-combating agents:

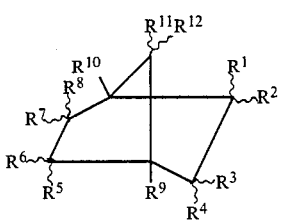

in which
- $R^1$ represents a hydrogen or halogen atom or a cyano, optionally substituted alkyl, optionally substituted aryl, carboxyl, optionally substituted alkoxycarbonyl, optionally substituted aryloxycarbonyl or optionally substituted aminocarbonyl group,
- $R^2$ represents a halogen atom or a cyano, nitro or halogenoalkyl group, $R^2$ representing CN, halogen or halogenoalkyl when $R^3$ or $R^4$ represents $CCl_3$,
- $R^3$ represents a hydrogen or halogen atom or an optionally substituted alkyl, optionally substituted aryl, nitro, hydroxyl, optionally substituted alkoxy, optionally substituted aryloxy, optionally substituted alkylthio, optionally substituted arylthio, acyloxy, alkylsulphonyl, arylsulphonyl, alkylsulphinyl, arylsulphinyl, cyano, optionally substituted alkoxycarbonyl, aralkoxycarbonyl or optionally substituted aryloxycarbonyl group,
- $R^4$ represents a hydrogen or halogen atom or an optionally substituted alkyl, optionally substituted aryl, nitro, halogen, optionally substituted alkoxy, optionally substituted aryloxy, optionally substituted alkylthio, optionally substituted arylthio, acyloxy, alkylsulphonyl, arylsulphonyl, alkylsulphinyl, arylsulphinyl, optionally substituted alkoxycarbonyl or optionally substituted aryloxycarbonyl group, or $R^3$ and $R^4$ together can represent an optionally substituted methylene group,
- $R^5$, $R^6$, $R^7$ and $R^8$ are identical or different, and independently of one another represent a hydrogen or halogen atom, an optionally substituted alkyl, optionally substituted aryl, cyano, optionally substituted alkoxycarbonyl, optionally substituted aryloxycarbonyl, alkoxy, aryloxy, optionally substituted alkylthio or optionally substituted arylthio group, and
- $R^6$ and $R^7$ together can represent a double bond or oxygen, or $R^5$ and $R^6$ and/or $R^7$ and $R^8$ together can represent an optionally substituted methylene group,
- $R^9$ and $R^{10}$ are identical or different, and independently of each other represent a hydrogen atom, an optionally substituted alkyl, optionally substituted aryl, cyano, optionally substituted alkoxycarbonyl, optionally substituted aryloxycarbonyl, alkoxy, aryloxy, optionally substituted alkylthio or optionally substituted arylthio group or a fluorine atom, and
- $R^{11}$ and $R^{12}$ independently of each other represent a hydrogen atom or an optionally substituted alkyl, optionally substituted aryl, halogen, cyano, optionally substituted alkoxycarbonyl, optionally substituted aryloxycarbonyl, alkoxy, aryloxy, optionally substituted alkylthio or optionally substituted arylthio group, or $R^{11}$ and $R^{12}$ together represent an oxygen or sulphur atom or an imino, alkylimino, arylimino or an optionally substituted methylene group.

The formula (I) embraces the stereoisomers and optical isomers which are possible in each case.

The present invention thus provides a pesticidal (especially insecticidal, acaricidal and rodenticidal) composition, characterized in that it contains as active ingredient a compound of formula (I), as defined above, in admixture with a solid or liquefied gaseous diluent or carrier or in admixture with a liquid diluent or carrier containing a surface-active agent.

According to the present invention we further provide a method for combating pests, characterized in that there is applied to the pests, or to a habitat thereof, a compound of formula (I), as defined above, alone or in the form of a composition containing as active ingredient a compound of formula (I), as defined above, in admixture with a diluent or carrier.

Surprisingly, the substituted bicyclic compounds of the formula (I) exhibit a better insecticidal action than the compounds known from the prior art. In addition, they are active as rodenticides.

Preferred compounds of formula (I) used as active compounds according to the invention are those in which,
- $R^1$ represents a hydrogen or halogen atom or a $C_1$ to $C_4$ alkyl, $C_1$ to $C_4$ halogenoalkyl, phenyl, cyano or aminocarbonyl group,
- $R^2$ represents a halogen atom or a cyano, nitro or $C_1$ to $C_4$ halogenoalkyl group, $R^2$ representing CN, halogen or halogenoalkyl when $R^3$ or $R^4$ represents $CCl_3$,
- $R^3$ represents a hydrogen atom, a $C_1$ to $C_4$ alkyl group, a phenyl group which is optionally substituted by halogen, alkyl or $NO_2$, a halogen atom or a $C_1$ to $C_4$ halogenoalkyl, acetoxy, $C_1$ to $C_4$ alkoxycarbonyl, aralkoxycarbonyl, phenoxycarbonyl, cyano, nitro, hydroxyl, $C_1$ to $C_4$ alkoxy or phenoxy group, $R^4$ represents a hydrogen atom, a $C_1$ to $C_4$ alkyl group, a phenyl group which is optionally substituted by halogen or $NO_2$, a halogen atom or a $C_1$ to $C_4$ halogenoalkyl or $C_1$ to $C_4$ alkoxycarbonyl group, or $R^3$ and $R^4$ together represent a dihalogenomethylene radical,
- $R^5$, $R^6$, $R^7$ and $R^8$ independently of one another represent a hydrogen atom or a $C_1$ to $C_4$ alkyl, phenyl, halogen, $C_1$ to $C_4$ halogenoalkyl, $C_1$ to $C_4$ alkylthio, phenylthio, phenoxy or $C_1$ to $C_4$ alkoxy group, and $R^5$ and $R^6$ together can represent a double bond or oxygen, $R^9$ and $R^{10}$ independently of each other represent a hydrogen atom, a $C_1$ to $C_4$ alkyl or $C_1$ to $C_4$ halogenoalkyl group or a fluorine atom, and $R^{11}$ and $R^{12}$ independently of each other represent hydrogen, $C_1$ to $C_4$ alkyl, $C_1$ to $C_4$ halogenoalkyl or halogen, or $R^{11}$ and $R^{12}$ together represent an ethylidene or isopropylidene radical.

Particularly preferred compounds of formula (I) used as active compounds according to the invention are those in which $R^1$ represents a hydrogen or fluorine atom or a cyano, methyl, ethyl or trifluoromethyl group, $R^2$ represents a fluorine atom or a cyano, trifluoromethyl, nitro or trichloromethyl group, $R^2$ representing CN, F, $CF_3$ or $CCl_3$ when $R^3$ or $R^4$ represents $CCl_3$, $R^3$ represents a hydrogen, bromine, chlorine or fluorine atom or a methyl, ethyl, cyano, trifluoromethyl, trichloromethyl, acetoxy, hydroxyl, dichlorofluoromethyl, chlorodifluoromethyl, bromodichloromethyl, phenyl, o-chlorophenyl, p-nitrophenyl, methoxycarbonyl, ethoxycarbonyl, pentafluorobenzyloxycarbonyl or phenoxycarbonyl group, $R^4$ represents a hydrogen, bromine, chlorine or fluorine atom or a methyl, ethyl, trifluoromethyl, trichloromethyl, dichlorofluoromethyl, chlorodifluoromethyl, bromodichloromethyl, phenyl, o-chlorophenyl, p-nitrophenyl, methoxycarbonyl or ethoxycarbonyl group, or $R^3$ and $R^4$ together represent a dichloromethylene radical, $R^5$, $R^6$, $R^7$ and $R^8$ independently of one another represent a hydrogen, bromine, chlorine or fluorine atom or a methyl, methylthio or phenylthio group, and $R^6$ and $R^7$ together can represent a double bond or oxygen, $R^9$ and $R^{10}$ independently of each other represent a hydrogen atom, a methyl or trifluoromethyl group of a fluorine atom, $R^{11}$ and $R^{12}$ independently of each other represent a hydrogen, fluorine, bromine or chlorine atom or a methyl, 1-bromoethyl, 1-chloroethyl, 1-bromo-1-methylethyl or 1-chloro-1-methylethyl group, or $R^{11}$ and $R^{12}$ together represent an ethylidene or isopropylidene radical.

The following active compounds may be mentioned individually: 3,3-dichloro-bicyclo[2,2,1]hept-5-ene-2,2-dicarbonitrile, 3,3-dichloro-bicyclo[2,2,1]heptane-2,2-dicarbonitrile, 3-chloro-bicyclo[2,2,1]hept-5-ene-2,2-dicarbonitrile, 3-chloro-bicyclo[2,2,1]heptane-2,2-dicarbonitrile, 5,6-dibromo-3,3-dichloro-bicyclo[2,2,1]heptane-2,2-dicarbonitrile, 3,3,5,6-tetrachloro-bicyclo[2,2,1]heptane-2,2-dicarbonitrile, 5-bromo-3,3-dichloro-bicyclo[2,2,1]hept-5-ene-2,2-dicarbonitrile, 6-bromo-3,3-dichlorobicyclo[2,2,1]hept-5-ene-2,2-dicarbonitrile, 3,3-dichloro-5,6-epoxy-bicyclo[2,2,1]heptane-2,2-dicarbonitrile, 2,2,3-trifluoro-3-trifluoromethyl-bicyclo[2,2,1]hept-5-ene, 3,3-bis-(trifluoromethyl)-bicyclo[2,2,1]hept-5-ene-2,2-dicarbonitrile, 3,3-bis-(trifluoromethyl)-bicyclo[2,2,1]heptane-2,2-dicarbonitrile, 3-chloro-3-trifluoromethyl-bicyclo[2,2,1]hept-5-ene-2,2-dicarbonitrile, bicyclo[2,2,1]hept-5-ene-2,2-dicarbonitrile, 3,3-dichloro-5,6-epoxy-bicyclo[2,2,1]heptane-2,2-dicarbonitrile, 3-acetoxy-bicyclo[2,2,1]hept-5-ene-2,2-dicarbonitrile, 3-chloromethyl-bicyclo[2,2,1]hept-5-ene-2,2-dicarbonitrile, bicyclo[2,2,1]heptane-2,2-dicarbonitrile, bicyclo[2,2,1]hept-5-ene-2-carbonitrile, 2-chloro-bicyclo[2,2,1]hept-5-ene-2-carbonitrile, methyl 3,3-dichloro-2-cyano-bicyclo[2,2,1]hept-5-ene-2-carboxylate, 3-chloro-2-cyano-bicyclo[2,2,1]hept-5-ene-2-carboxylic acid amide, 2,3-dichloro-bicyclo[2,2,1]hept-5-ene-2,3-dicarbonitrile and 5,6-dibromo-3-chloro-bicyclo[2,2,1]heptane-2,2-dicarbonitrile, 5,6-dibromo-3,3-bis(trifluoromethyl)-bicyclo[2,2,1]-heptane-2,2-dicarbonitrile.

Compounds of the general formula (I) are known, and they can be prepared according to generally known methods.

The present invention, however, also provides, as new compounds, the compounds of the general formula

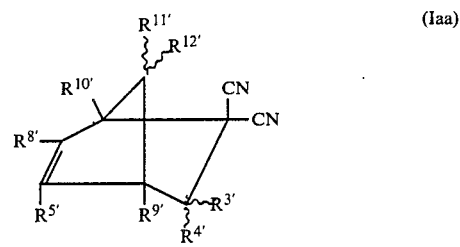

(Iaa)

wherein $R^{3'}$ represents a chlorine, bromine or fluorine atom or a $C_1$ to $C_4$ alkyl, trifluoromethyl or acetoxy group, $R^{4'}$ represents a hydrogen, bromine or fluorine atom or a methyl or optionally substituted phenyl group, $R^{5'}$, $R^{8'}$, $R^{9'}$, $R^{10'}$, $R^{11'}$ and $R^{12'}$ independently of one another represent a hydrogen atom, a methyl, ethyl, hydroxymethyl, halogenomethyl or trifluoromethyl group or a fluorine atom, and $R^{11'}$ and $R^{12'}$ additionally together can represent a substituted methylene group or an oxygen atom.

According to the present invention we further provide a process for the production of a compound of formula (Iaa) according to the invention, characterized in that cyclopentadiene of the general formula

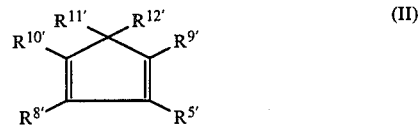

(II)

as a monomer or dimer,
wherein $R^{5'}$, $R^{8'}$, $R^{9'}$, $R^{10'}$, $R^{11'}$ and $R^{12'}$ have the meanings given above,
is reacted with an alkene of the general formula

(III)

wherein $R^{3'}$ and $R^{4'}$ have the meanings given above.

In this process, generally, the olefin of the formula (III), if appropriate in a solvent, is mixed with the cyclopentadiene of the formula (II), or the two components, if appropriate in a solvent, are added dropwise together.

The following solvents are suitable; alkanes (such as pentane, hexane, petroleum ether and logroin), cycloalkanes (such as cyclohexane), aromatic compounds (such as benzene, toluene, xylene and chlorobenzene), cyclic ethers (such as tetrahydrofuran and dioxane) and halogenohydrocarbons (such as dichloromethane, trichloromethane and tetrachloromethane).

The reaction is generally carried out at a temperature between −20° C. and 250° C., preferably between 20° and 100° C.

The cyclopentadiene of formula (II) is preferably employed as a monomer, in a molar ratio of 1:1 to 1:10, preferably 1:1 to 1:3, relative to the olefin of formula (III). In the case of a reaction temperature of above 120° C., preferably 150° C. or above, a dimer of the cyclopentadiene of formula (II) can also be employed.

The invention further provides, as new compounds, compounds of the general formula

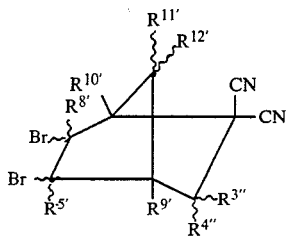

(Ib)

in which
$R^{5'}$, $R^{8'}$, $R^{9'}$, $R^{10'}$, $R^{11'}$ and $R^{12'}$ have the meaning given above,
$R^{3''}$ represents a chlorine, bromine or fluorine atom or a $C_1$ to $C_4$ alkyl, trifluoromethyl, acetoxy, optionally substituted phenyl or cyano group and $R^{4''}$ represents a hydrogen, chlorine, bromine or fluorine atom or a $C_1$ to $C_4$ alkyl, trifluoromethyl or optionally substituted phenyl group.

According to the present invention we provide a process for the production of a compound of formula (Ib), characterized in that a compound of the general formula

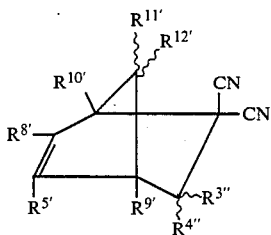

(Ia)

in which $R^{3''}$, $R^{4''}$, $R^{5'}$, $R^{8'}$, $R^{9'}$, $R^{10'}$, $R^{11'}$ and $R^{12'}$ have the meanings given above,
is reacted with bromine, if appropriate in a solvent.

The bromine is generally added dropwise, if appropriate in the same solvent, in a molar ratio of 1:1 to 1:10, preferably 1:1 to 1:3, relative to the compound of formula (Ia). Suitable solvents are: chlorinated hydrocarbons (such as dichloromethane, trichloromethane and tetrachloromethane), alkanes (such as pentane and hexane) and acetic acid.

The reaction is carried out at a temperature between 0° C. and 100° C., preferably between 20° C. and 80° C. After the reaction is complete, the solvent and, if appropriate, excess bromine are distilled off, and the residue is distilled or recrystallized.

The present invention further provides, as new compounds, the compounds of the general formula

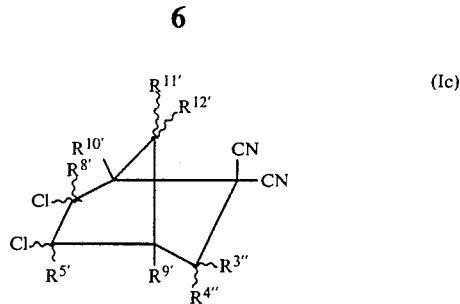

(Ic)

in which $R^{3''}$, $R^{4''}$, $R^{5'}$, $R^{8'}$, $R^{9'}$, $R^{10'}$, $R^{11'}$ and $R^{12'}$ have the meanings given above.

According to the present invention we provide a process for the production of a compound of formula (Ic), characterized in that a compound of the general formula (Ia), as defined above, is reacted with chlorine.

The reaction is preferably carried out in a chlorinated hydrocarbon (such as dichloromethane, trichloromethane or tetrachloromethane) and at a temperature between 0° C. and 100° C., preferably between 20° and 80° C. In this process, a stream of chlorine is generally passed through the mixture until the compound of the formula (Ia) is completely converted. If appropriate, the reaction may be supported by exposing the reaction mixture to a UV or daylight lamp. The solvent is distilled off, and the residue is distilled or recrystallized.

The present invention further provides, as new compounds, the compounds of the general formula

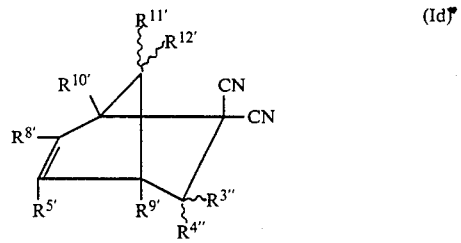

(Id)

in which
$R^{3''}$ and $R^{4''}$ have the meanings given above,
$R^{5''}$, $R^{8''}$, $R^{9'}$, $R^{10'}$, $R^{11'}$ and $R^{12'}$ independently of one another represent a hydrogen atom, a methyl, ethyl, hydroxymethyl, halogenomethyl or trifluoromethyl group or a fluorine atom, and
$R^{11'}$ and $R^{12'}$ additionally together can represent a substituted methylene group or an oxygen atom;
one of the radicals $R^{5''}$ and $R^{8''}$ representing a bromine atom and the other having the meaning given.

According to the present invention we further provide a process for the production of a compound of formula (Id), characterized in that a compound of the formula (Ib), as defined above, with at least one of the radicals $R^{5'}$ and $R^{8'}$ representing a hydrogen atom, if appropriate in a solvent, is dehydrobrominated using a base.

Suitable solvents are chlorinated hydrocarbons (such as dichloromethane, trichloromethane and tetrachloromethane), aromatic compounds (such as benzene, toluene, xylene and chlorobenzene), alkanes (such as pentane and hexane) and cyclic ethers (such as tetrahydrofuran and dioxane).

Suitable bases are amines, preferably tertiary amines (such as triethylamine, diazabicycloundecene, diazabicyclononene, diisopropylethylamine, pyridine and quinoline).

The reaction is carried out at a temperature between 0° and 120° C., preferably between 20° C. and 80° C.

The molar ratio of the compound of formula (Ib) to the amine is generally from 1:1 to 1:10, preferably 1:1 to 1:3. The resulting ammonium bromide is separated off, for example with aqueous hydrochloric acid, and the product is isolated from the organic phase.

The present invention further provides, as new compounds, compounds of the general formula

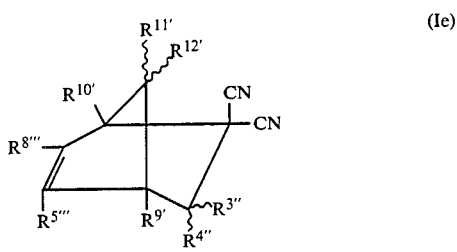
(Ie)

in which
R$^{3''}$ and R$^{4''}$ have the meanings given above,
R$^{5'''}$, R$^{8'''}$, R$^{9'}$, R$^{10'}$, R$^{11'}$ and R$^{12'}$ independently of one another represent a hydrogen atom, a methyl, ethyl, hydroxymethyl, halogenomethyl or trifluoromethyl group or a fluorine atom, and
R$^{11'}$ and R$^{12'}$ additionally together can represent a substituted methylene group or an oxygen atom;
one of the radicals R$^{5'''}$ and R$^{8'''}$ representing a chlorine atom and the other having the meaning given.

According to the present invention we further provide a process for the production of a compound of formula (Ie), characterized in that a compound of formula (Ic), as defined above, with at least one of the radicals R$^{5'}$ and R$^{8'}$ representing a hydrogen atom, if appropriate in a solvent, is dehydrochlorinated using a base.

The solvent, base and reactions conditions here are analogous to those mentioned previously for the dehydrobromination of compounds of formula (Ib).

The present invention further provides, as new compounds, compounds of the general formula

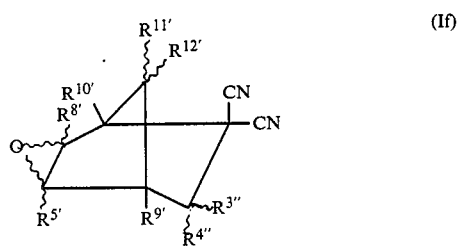
(If)

in which R$^{3''}$, R$^{4''}$, R$^{5'}$, R$^{8'}$, R$^{9'}$, R$^{10'}$, R$^{11'}$ and R$^{12'}$ have the meanings given above.

According to the present invention we further provide a process for the production of a compound of formula (If), characterized in that a compound of formula (Ia), as defined above is reacted with a per-acid.

The reaction is preferably carried out in a chlorinated hydrocarbon (such as dichloromethane or trichloromethane) or in an aromatic compound (such as benzene, toluene or chlorobenzene). For this purpose, a solution of, for example, m-chloroperbenzoic acid may be added dropwise at a temperature of between 0° C. and 130° C., in the ratio of 1:1 to 1:2. The working-up is effected in a customary manner, using sodium bicarbonate/sodium bisulphite solution to separate off the excess per-acid and the m-chlorobenzoic acid formed. The product (If) is in the organic phase. The epoxidation can be carried out using other per-acids, such as peracetic acid or perpropionic acid.

The present invention further provides, as new compounds of the general formula

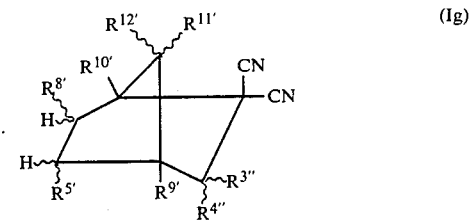
(Ig)

in which R$^{3''}$, R$^{4''}$, R$^{5'}$, R$^{8'}$, R$^{9'}$, R$^{10'}$, R$^{11'}$ and R$^{12'}$ have the meanings given above.

According to the present invention we provide a process for the production of a compound of formula (Ig), characterized in that a compound of formula (Ia) is catalytically hydrogenated in a solvent.

Examples of suitable solvents are: ethyl acetate, tetrahydrofuran, dioxane and cyclohexane.

Supported noble metals (such as platinum on carbon or palladium black) may be used as catalysts.

The reaction is generally carried out at a temperature between 20° C. and 100° C. and under a pressure of from 1 to 10 bar.

The present invention further provides, as new compounds, compounds of the general formula

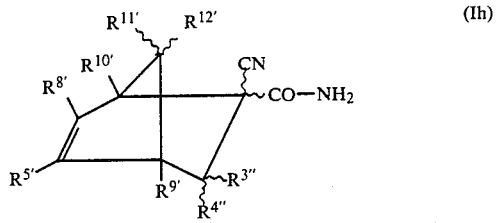
(Ih)

in which R$^{3''}$, R$^{4''}$, R$^{5'}$, R$^{8'}$, R$^{9'}$, R$^{10'}$, R$^{11'}$ and R$^{12'}$ have the meanings given above.

According to the present invention we further provide a process for the production of a compound of formula (Ih) characterized in that a compound of the general formula (Ia), as defined above, is partially hydrolyzed.

The reaction conditions for the mentioned partial hydrolysis are in themselves known.

The active compounds are well tolerated by plants, have a favorable level of toxicity to warm-blooded animals, and are suitable for combating arthropod pests, especially insects and arachnida, which are encountered in agriculture, in forestry, in the protection of stored products and of materials, and in the hygiene field. They are active against normally sensitive and resistant species and against all or some stages of development.

The abovementioned pests include:
from the class of the Isopoda, for example *Oniscus asellus, Armadillidium vulgare* and *Porcellio scaber;*
from the class of the Diplopoda, for example *Blaniulus guttulatus;*
from the class of the Chilopoda, for example *Geophilus carpohagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp, *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretalla, Cacoecia podana, Capua reticulana, Choristoneura fumiferana, Clysia ambiguella Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp, Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Ambylomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The substances according to the invention possess rodenticidal properties, and are therefore suitable for combating leporine animals (Lagomorpha) and rodents (Rodentia), such as those of the squirrel species (Sciuroidae), pocket gophers (Geomyoidae) and those of the mouse species (Muroidae), which essentially comprises animals of the dormouse species (Muscardinidae) and the mice (Muridae).

The leporine animals essentially comprise the Leporidae, such as the rabbit (*Oryctolagus cuniculus*)*, those of the squirrel species include, for example, the suslik (*Citellus citellus*)* and the ground squirrel (*Citellus lateralis*)*, and the pocket gophers include, for example, the mountain pocket gopher (*Thomomys talpoides*)*.

The animals of the dormouse species include, for example, the edible dormouse (*Glis glis*)*.

The mice essentially comprise, in the group of the long-tailed mice (Murinae), the wood mice (Apodemus spec.); the rats (Rattus spec.), such as the black rat (*Rattus rattus*)* and the brown rat (*Rattus norvegicus*)*; and the common mice (Mus spec.), such as *Mus musculus**; and in the group comprising the animals of the hamster species (Cricetinae), the European hamster (*Cricetus cricetus*)*, and in the group comprising the short-tailed mice (Microtinae), for example the fieldmouse (*Microtus arvalis*)*, the field vole (*Microtus agrestis*)*, the water vole (*Arvicola terrestris*)* and the muskrat (*Ondatra zibethica*).

In the above list, those pests indicated "*" are particularly important as pests to be combated.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarobns, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against pests harmful to health and pests of stored products, the active compounds are distinguished by an excellent residual action on wood and clay as well as a good stability to alkali on limed substrates.

As indicated previously, the active compounds according to the invention are also suitable as rodenticides.

PREPARATIVE EXAMPLES

Example 1

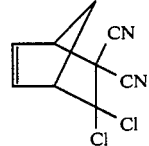

IV 100 g (1.52 mols) of monomeric cyclopentadiene are dissolved in 300 ml of tetrahydrofuran, and 220 g (1.50 mols) of 2,2-dichloro-1-cyano-acrylonitrile in 1 liter of tetrahydrofuran are added dropwise. The mixture is allowed to stand for 10 hours at 25° C., and the solvent is distilled off. The residue can be recrystallized from ethanol. 265 g (83%) of 3,3-dichloro-bicyclo[2,2,1]hept-5-ene-2,2-dicarbonitrile, m.p. 161° C., are obtained.

Example 2

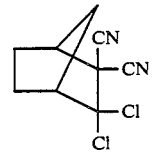

V 30 g (0.14 mol) of the (IV) prepared in Example 1 are dissolved in 170 ml of ethyl acetate, the solution is introduced into an autoclave, and 2 g of 1% strength platinum on carbon are added. The mixture is warmed to 40° C., and hydrogen is forced in until a pressure of 10 bar is reached. After approx. 2 hours, the reaction is complete. The catalyst is filtered off and the solvent is evaporated. 30 g (99%) of 3,3-dichlorobicyclo[2,2,1]heptane-2,2-dicarbonitrile, m.p. 148° C., are obtained.

Example 3

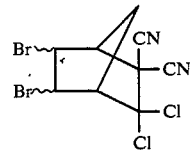

VI 100 g (0.47 mol) of the (IV) prepared in Example 1 are dissolved in 500 ml of trichloromethane, and 75 g (0.47 mol) of bromine in 100 ml of trichloromethane are added dropwise. The mixture is heated under reflux until the color of the bromine disappears. The solvent is distilled off, and 175 g (100%) of 5,6-dibromo-3,3-dichloro-bicyclo[2,2,1]heptane-2,2-dicarbonitrile remain, m.p. 133° C.

Example 4

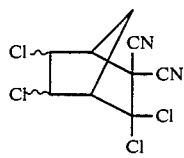
VII 100 g (0.47 mol) of the (IV) prepared in Example 1 are dissolved in 500 ml of chloroform, and the solution is heated to the boil. Chlorine gas is passed through the solution until, according to gas chromatographic analysis, the starting compound has been completely converted. 130 g (98%) of 3,3,5,6-tetrachlorobicyclo[2,2,1]heptane-2,2-dicarbonitrile, m.p. 126° C. (from ethanol), are obtained.

Example 5

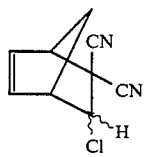
VIII 50 g (0.44 mol) of 2-chloro-1-cyano-acrylonitrile and 30 g (0.45 mol) of monomeric cyclopentadiene are dissolved in 500 ml of tetrahydrofuran, and the solution is left for 15 hours at 25° C. The volatile constituents are stripped off in vacuo, and the product is recrystallized from ethanol. 56 g (71%) of 3-chlorobicyclo[2,2,1]hept-5-ene-2,2-dicarbonitrile are obtained. The product consists of a mixture of the exo compound (VIII a) and the endo compound (VIII b).

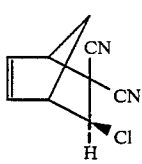
VIIIa

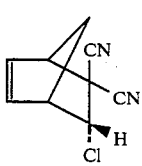
VIIIb

Pure VIII b can be obtained by fractional crystallization from ethanol (m.p. 131°-133° C.).

Example 6

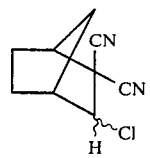
IX 30 g (0.17 mol) of the (VIII) prepared according to Example 5 are dissolved in 170 ml of ethyl acetate, the solution is introduced into an autoclave, 3 g of 1% strength platinum on carbon are added, the mixture is warmed to 50° C., and hydrogen is forced in until a pressure of 15 bar is reached. After 1 hour, the pressure in the autoclave is released, the catalyst is filtered off, and the filtrate is concentrated in a rotary evaporator. 30 g (99%) of 3-chloro-bicyclo[2,2,1]heptane-2,2-dicarbonitrile remain, m.p. 131° C.

Example 7

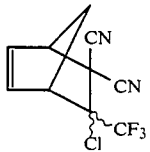
X 50 g (0.28 mol) of 2-chloro-1-cyano-2-trifluoromethyl-acrylonitrile and 18.5 g (0.28 mol) of monomeric cyclopentadiene in 200 ml of dioxane are kept at 25° C. for 15 hours. The solvent is stripped off, and 65 g (95%) of 3-chloro-3-trifluoromethyl-bicyclo[2,2,1]hept-5-ene-2,2-dicarbonitrile, m.p. 173° C. (from ethanol), are obtained.

Example 8

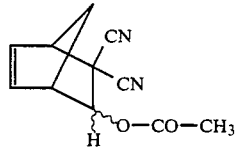
XI 20 g (0.15 mol) of 2-acetoxy-1-cyano-acrylonitrile and 15 g (0.23 mol) of monomeric cyclopentadiene in 150 ml of tetrahydrofuran are kept at 25° C. for 16 hours. All volatile constituents are stripped off in vacuo, and 26 g (87%) of 3-acetoxy-bicyclo[2,2,1]hept-5-ene-2,2-dicarbonitrile, m.p. 133° C. (from tetrahydrofuran), are obtained.

Example 9

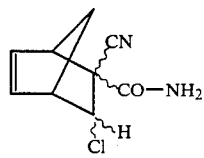
XII 20 g (0.11 mol) of the VIII prepared in Example 5 are dissolved in 300 ml of 2% strength ethanolic potassium hydroxide solution, and the solution is heated under reflux for 2 hours. The mixture is worked up in the customary manner with water/ether, and 19 g (78%) of 3-chloro-2-cyano-bicyclo[2,2,1]hept-5-ene-2-carboxylic acid amide, m.p. 141°–143° C. (from ethanol), are obtained.

Example 10

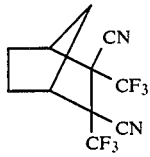

XIII 10 g (0.036 mol) of 3,3-bis-trifluoromethylbicyclo[2,2,1]hept-5-ene-2,2-dicarbonitrile (W. J. Middleton, J. Org. Chem. 30, 1402 (1965)) are dissolved in 150 ml of ethyl acetate, and the solution is introduced into an autoclave. 2 g of 5% strength Pt/C are introduced, the mixture is warmed to 27° C., and hydrogen is forced in until a pressure of 7 bar is reached. After 15 minutes, the pressure in the autoclave is released, the catalyst is filtered off, and the filtrate is concentrated in a rotary evaporator. 10 g (99%) of 3,3-bis-trifluoromethyl-bicyclo[2,2,1]heptane-2,2-dicarbonitrile remain, m.p. 178° C.

Example 11

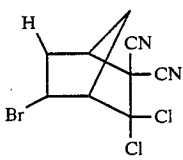

XIVa

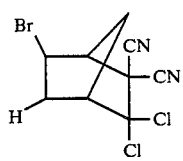

XIVb 50 g (0.13 mol) of the (VI) prepared in Example 3 are dissolved in 300 ml of toluene, and 30.4 g (0.20 mol) of diazabicycloundecene (DBU) in 200 ml of toluene are added dropwise. The mixture is heated at the boil for 1 hour, is cooled, and is extracted by shaking with 1N hydrochloric acid. The organic phase is dried with magnesium sulphate and is concentrated in a rotary evaporator. 30.5 g (78%) of a mixture of 5-bromo-3,3-dichloro-bicyclo[2,2,1]hept-5-ene-2,2-dicarbonitrile (XIVa) and 6-bromo-3,3-dichloro-bicyclo[2,2,1]hept-5-ene-2,2-dicarbonitrile (XIVb) remain, melting range 105°–107° C.

Example 12

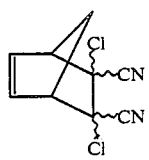

XV 80 g (0.54 mol) of 1,2-dichloro-2-cyano-acrylonitrile and 44 g (0.67 mol) of monomeric cyclopentadiene in 1 l of tetrahydrofuran are heated under reflux for 9 hours. The volatile constituents are stripped off in vacuo, and 58 g (50%) of 2,3-dichloro-bicyclo[2,2,1]hept-5-ene-2,3-dicarbonitrile, m.p. 159° C. (from ethanol), are obtained.

Example 13

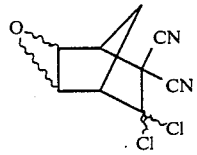

XVI 21 g (0.1 mol) of the (IV) prepared in Example 1 are dissolved in 100 ml of chlorobenzene, and 20 g (0.12 mol) of m-chloroperbenzoic acid in 200 ml of chlorobenzene are added dropwise. The mixture is heated under reflux for 4 hours, and is worked up in the customary manner with sodium bisulphite solution to destroy the excess of per-acid, and sodium bicarbonate solution to separate off the m-chlorobenzoic acid. From the organic phase, 17 g (75%) of 3,3-dichloro-5,6-epoxybicyclo[2,2,1]heptane-2,2-dicarbonitrile were isolated, m.p. 229° C.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The pesticidal activity of compounds of this invention is illustrated by the following biotest examples.

Example 14

$LT_{100}$ test for Diptera

Test insects: *Musca domestica*

Solvent: acetone 2 parts by weight of active compound were taken up in 1,000 parts by volume of solvent. The solution thus obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound used. About 25 test insects were then placed in the Petri dish and the dish was covered with a glass lid.

The condition of the test insects was continuously checked. The time which was necessary for a 100% knock-down effect was determined.

The test insects, the active compounds, the concentrations of the active compounds and the periods of time at which there was a 100% knock-down effect can be seen from the table which follows:

TABLE

LT₁₀₀ test for Diptera (*Musca domestica*)

| Active compounds | Concentration of the active compound in the solution in % | LT₁₀₀ |
|---|---|---|
| Known: | | |
| Toxaphene | 0.2 | 4 hours = 0% |
| | 0.02 | 6 hours = 90% |
| According to the invention: | | |
| 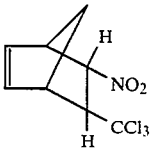 | 0.002 | 90' |
| 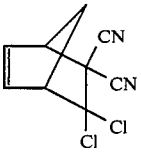 | 0.02 | 110' |
| 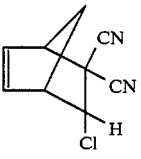 | 0.02 | 85' |
| 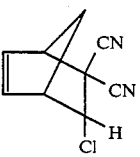 | 0.02 | 110' |
| 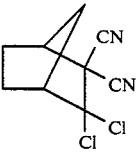 | 0.002 | 150' |
| 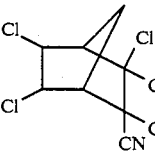 | 0.02 | 55' |
| 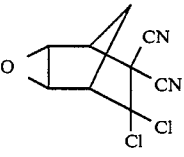 | 0.0002 | 75' |
| 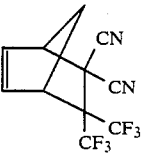 | 0.02 | 90' |
|  | 0.02 | 65' |
| 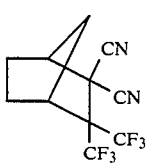 | 0.02 | 90' |

Example 15

LT₁₀₀ test for Diptera

Test insects: *Aedes aegypti*

Solvent: acetone 2 parts by weight of active compound were taken up in 1,000 parts by volume of solvent. The solution thus obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound used. About 25 test insects were then placed in the Petri dish and the dish was covered with a glass lid.

The condition of the test insects, was continuously checked. The time which was necessary for a 100% knock-down effect was determined.

The test insects, the active compounds, the concentrations of the active compounds and the periods of time at which there was a 100% knock-down effect can be seen from the table which follows:

TABLE

LT₁₀₀ test for Diptera (*Aedes aegypti*)

| Active compounds | Concentration of the active compound in the solution in % | LT₁₀₀ |
|---|---|---|
| Known: | | |
| Toxaphene | | |

TABLE-continued

LT₁₀₀ test for Diptera (*Aedes aegypti*)

| Active compounds | Concentration of the active compound in the solution in % | LT₁₀₀ |
|---|---|---|
| 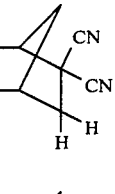 H, NO₂, CCl₃, H | 0.02 | 180' |

According to the invention:

| Active compounds | Concentration of the active compound in the solution in % | LT₁₀₀ |
|---|---|---|
| 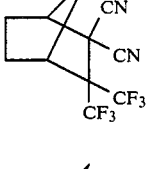 CN, CN, Cl | 0.002 | 60' |
| CN, CN endo/exo mixture, H, Cl | 0.002 | 120' |
| CN, CN 90% endo + 10% exo, H, Cl | 0.002 | 120' |
| CN, CN, Cl, Cl | 0.002 | 120' |
| Cl, Cl, Cl, Cl, CN, CN | 0.002 | 60' |
| O, CN, CN, Cl | 0.002 | 60' |
| CN, CN, CF₃, CF₃ | 0.002 | 60' |

TABLE-continued

LT₁₀₀ test for Diptera (*Aedes aegypti*)

| Active compounds | Concentration of the active compound in the solution in % | LT₁₀₀ |
|---|---|---|
| CN, CN, H | 0.02 | 60' |
| CN, CN, CF₃, CF₃ | 0.02 | 60' |
| CN, CN | 0.02 | 60' |
| CN | 0.02 | 120' |
| Cl, CN, Cl, CN | 0.02 | 120' |
| Br, Cl, Cl, Br, CN | 0.02 | 60' |
| CN, CN, H, Cl | 0.02 | 60' |
| Br, CN, CN, Cl | 0.02 | 60' |
| CN, CD₂CH₃, Cl | 0.02 | 120' |

TABLE-continued
LT₁₀₀ test for Diptera (Aedes aegypti)

| Active compounds | Concentration of the active compound in the solution in % | LT₁₀₀ |
|---|---|---|
|  | 0.02 | 60' |

Example 16

Drosophila test
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

1 cm³ of the preparation of the active compound was pipetted onto a filter paper disc (7 cm diameter). The wet disc was placed over the opening of a glass vessel containing 50 vinegar flies (*Drosophila melanogaster*) and was covered with a glass plate.

After the specified periods of time, the destruction in % was determined. 100% meant that all the flies had been killed; 0% meant that none of the flies had been killed.

The test insects, the active compounds, the concentration of the active compounds and the % destruction after 1 day can be seen from the table which follows:

TABLE
(Plant-damaging insects)
Drosophila test

| Active compounds | | Active compound concentration in % | Degree of destruction in % after 1 day |
|---|---|---|---|
| Toxaphene (known) | | 0.1 | 0 |
| 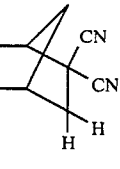 | exo/endo | 0.1 | 100 |
| 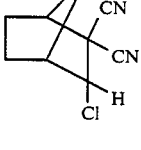 | exo/endo | 0.1 | 100 |
| 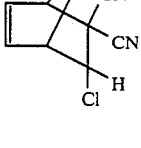 | | 0.1 | 100 |

TABLE-continued
(Plant-damaging insects)
Drosophila test

| Active compounds | | Active compound concentration in % | Degree of destruction in % after 1 day |
|---|---|---|---|
| 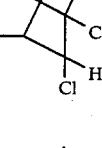 | | 0.1 | 100 |
| 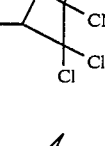 | exo/endo | 0.1 | 100 |
| 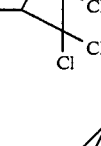 | exo/endo | 0.1 | 100 |
|  | 90% endo/ 10% exo | 0.1 | 100 |
| 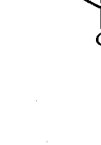 | | 0.1 | 100 |
| | | 0.1 | 100 |
| | | 0.1 | 100 |
| | | 0.1 | 100 |

TABLE-continued (Plant-damaging insects)
Drosophila test

| Active compounds | Active compound concentration in % | Degree of destruction in % after 1 day |
|---|---|---|
| 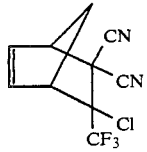 | 0.1 | 100 |
| 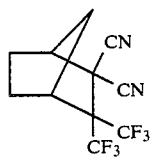 | 0.1 | 100 |
| 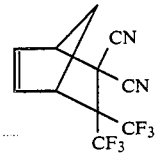 | 0.1 | 100 |
| 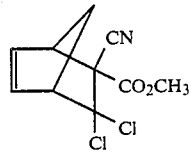 | 0.1 | 100 |
| 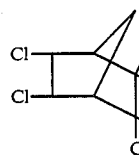 | 0.1 | 100 |
| 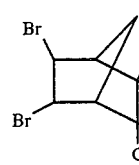 | 0.1 | 100 |
| 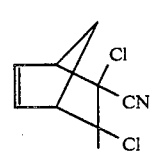 | 0.1 | 100 |
| 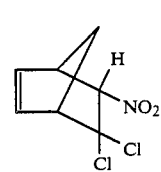 | 0.1 | 100 |

TABLE-continued (Plant-damaging insects)
Drosophila test

| Active compounds | Active compound concentration in % | Degree of destruction in % after 1 day |
|---|---|---|
| 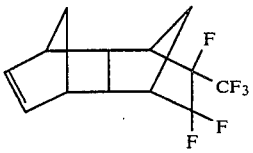 | 0.1 | 100 |
| 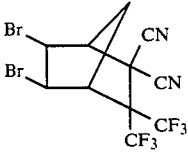 | 0.1 | 100 |

Example 17

Doralis test (systemic action)
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were each watered with 20 ml of the preparation of the active compound of the desired concentration in such a way that the preparation of the active compound penetrated into the soil without wetting the shoot. The active compound was taken up by the roots and passed to the shoot.

After the specified periods of time, the destruction in % was determined. 100% meant that all the aphids had been killed; 0% meant that none of the aphids had been killed.

The test insects, the active compounds, the concentration of the active compounds and the % destruction after 1 day can be seen from the table which follows:

TABLE (Plant-damaging insects)
*Doralis fabae* test (systemic action)

| Active compounds | Active compound concentration in % | Degree of destruction in % after 4 days |
|---|---|---|
| Toxaphene (known) | 0.1 | 0 |
| 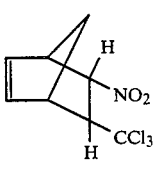 (known) | 0.1 | 0 |

TABLE-continued

(Plant-damaging insects)
*Doralis fabae* test (systemic action)

| Active compounds | Active compound concentration in % | Degree of destruction in % after 4 days |
|---|---|---|
| [structure: norbornene with CN, CN, Cl, Cl] | 0.1 | 100 |
| [structure: norbornene with CN, CN, Cl, CF₃] | 0.1 | 100 |
| [structure: Cl, Cl, Cl, Cl, CN, CN norbornane] | 0.1 | 85 |

Example 18

Tetranychus test (resistant)

Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean pants (*Phaseolus vulgaris*) which were heavily infested with the common spider mite or two-spotted spider mite (*Tetranychus urticae*) in all stages of development were treated by being dipped into the preparation of the active compound of the desired concentration.

After the specified periods of time, the destruction in % was determined. 100% meant that all the spider mites had been killed; 0% meant that none of the spider mites had been killed.

The test insects, the active compounds, the concentration of the active compounds and the % destruction after 2 days can be seen from the table which follows:

TABLE

(Plant-damaging mites)
Tetranychus test

| Active compounds | Active compound concentration in % | Degree of destruction in % after 2 days |
|---|---|---|
| Toxaphene (known) | 0.1 | 98 |
| | 0.01 | 0 |

TABLE-continued

(Plant-damaging mites)
Tetranychus test

| Active compounds | Active compound concentration in % | Degree of destruction in % after 2 days |
|---|---|---|
| [structure: Cl, Cl, Cl, Cl, CN, CN norbornane] | 0.1 | 100 |
| | 0.01 | 35 |

Example 19

Critical concentration test/soil insects

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The soil was filled into pots and the pots were left to stand at room temperature.

After 24 hours, the test insects were introduced into the treated soil, and after a further 2 to 7 days the degree of effectiveness of the active compound was determined in % by counting the dead and live test insects. The degree of effectiveness was 100% if all the test insects had been killed and was 0% if just as many test insects were still alive as in the case of the untreated control.

The active compounds, the amounts used and the results can be seen in the table which follows:

TABLE

| Active compound (constitution) | Degree of destruction in % in active compound concentration in ppm 10 |
|---|---|
| Toxaphene (known) | 10% |
| [structure: norbornene with Cl, Cl, CN, CN] | 100% |
| [structure: Cl, Cl, Cl, Cl, CN, CN norbornane] | 100% |

TABLE-continued

| Active compound (constitution) | Degree of destruction in % in active compound concentration in ppm 10 |
|---|---|
| 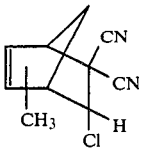 | 100% |
| 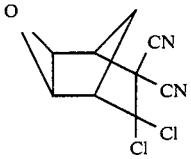 | 100% |
| 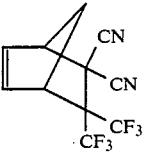 | 100% |
| 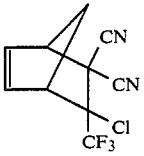 | 100% |
| 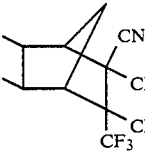 | 100% |

EXAMPLE 20

Critical concentration test/soil insects
Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The soil was filled into pots and the pots were left to stand at room temperature.

After 24 hours, the test insects were introduced into the treated soil, and after a further 7 days the degree of effectiveness of the active compound was determined in % by counting the dead and live test insects. The degree of effectiveness was 100% if all the test insects had been killed and was 0% if just as many test insects were still alive as in the case of the untreated control.

The active compounds, the amount used and the results can be seen in the table which follows:

TABLE

Soil insecticides
*Tenebrio molitor* larvae in the soil

| Active compound (constitution) | Degree of destruction in % at an active compound concentration in ppm of 10 |
|---|---|
| Toxaphene (known) | 0% |
| 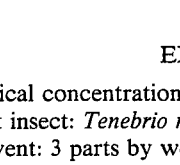 | 100% |
| 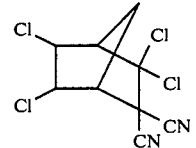 | 100% |
| 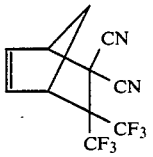 | 100% |
| 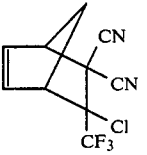 | 100% |

It will be appreciated that the instant specification and examples are set forth by way of illustration and not limitation, and that various modifications and changes may be made without departing from the spirit and scope of the present invention.

We claim:

1. A method of combating arthropods comprising applying to such arthropods an arthropodicidally effective amount of a substituted bicyclic compound of the formula

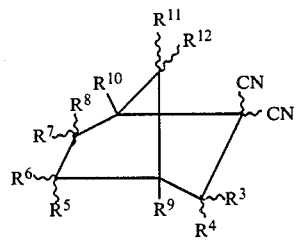

in which
$R^3$ represent hydrogen, $C_1$-$C_4$-alkyl, phenyl, phenyl substituted with halogen or $NO_2$, halogen, $C_{1-4}$-halogenoalkyl, acetoxy, $C_1$-$C_4$-alkoxycarbonyl, pentafluorobenzyloxycarbonyl, phenyloxycarbonyl, cyano, nitro, hydroxyl, C₁–C₄-alkoxy or phenyloxy, R⁴ represents hydrogen, C₁–C₄-alkyl, phenyl, phenyl substituted with halogen or NO₂, halogen, C₁₋₄-halogenoalkyl, C₁₋₄-alkoxycarbonyl or R³ and R⁴ together represent dihalogenomethylene, R⁵, R⁶, R⁷ and R⁸ independently of one another represent hydrogen, C₁–C₄-alkyl, phenyl, halogen, C₁₋₄-halogenoalkyl, C₁₋₄-alkylthio, phenylthio, phenoxy or C₁–C₄-alkoxy or R⁶ and R⁷ together represent a double bond or oxygen, R⁹ and R¹⁰ independently of one another represent hydrogen, C₁–C₄-alkyl, C₁₋₄-halogenoalkyl or fluorine, R¹¹ and R¹² independently of one another represent hydrogen, C₁₋₄-alkyl, C₁₋₄-halogenoalkyl, halogen or R¹¹ and R¹² together represent ethylidene or isopropylidene.

2. The method according to claim 1, in which said compound is 3,3-dichloro-bicyclo[2,2,1]hept-5-ene-2,2-dicarbonitrile of the formula

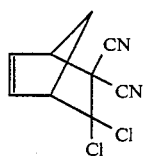

3. The method according to claim 1, in which said compound is 3,3,5,6-tetrachloro-bicyclo[2,2,1]heptane-2,2-dicarbonitrile of the formula

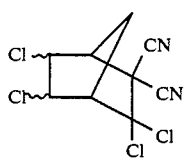

4. The method according to claim 1, in which said compound is 3,3-dichloro-5,6-epoxy-bicyclo[2,2,1]heptane-2,2-dicarbonitrile of the formula

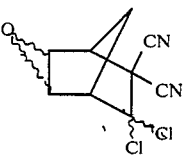

5. The method according to claim 1, in which said compound is 3,3-bis-(trifuloromethyl)-bicyclo[2,2,1]hept-5-ene-2,2-dicarbonitrile of the formula

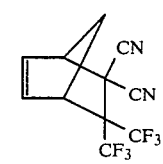

6. The method according to claim 1, in which said compound is bicyclo-[2,2,1]hept-5-ene-2,2-dicarbonitrile of the formula

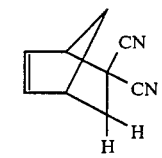

7. The method according to claim 1, in which said compound is 5,6-dibromo-3,3-bis(trifluoromethyl)-bicyclo-[2,2,1]-heptane-2,2-dicarbonitrile of the formula

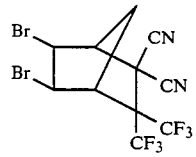

* * * * *